United States Patent [19]
Crooks et al.

[11] Patent Number: 5,552,440
[45] Date of Patent: Sep. 3, 1996

[54] USE OF L-CANAVANINE AS A CHEMOTHERAPEUTIC AGENT FOR THE TREATMENT OF PANCREATIC CANCER

[75] Inventors: Peter A. Crooks; Gerald A. Rosenthal, both of Lexington, Ky.

[73] Assignee: The University of Kentucky Research Foundation, Lexington, Ky.

[21] Appl. No.: 353,270

[22] Filed: Dec. 5, 1994

[51] Int. Cl.$^6$ ............... A61K 31/185; A61K 31/70
[52] U.S. Cl. ................................. 514/553; 514/50
[58] Field of Search ........................ 514/553, 50

[56] References Cited

PUBLICATIONS

Merck Index, 9th ed. p. 221, #1741, 1976.
Lewis, Medical Botany, Wiley & Sons, NY, p. 362, 1977.

*Primary Examiner*—John W. Rollins
*Attorney, Agent, or Firm*—Lowe, Price, LeBlanc & Becker

[57] ABSTRACT

A pharmaceutical composition of canavanine, and a method treatment of cancer, particularly pancreatic cancer with L-canavanine is disclosed.

7 Claims, 5 Drawing Sheets

USE OF L-CANAVANINE AS A CHEMOTHERAPEUTIC AGENT FOR THE TREATMENT OF PANCREATIC CANCER

TECHNICAL FIELD

The invention relates to a pharmaceutical composition comprising canavanine, and a method treatment of cancer, particularly pancreatic cancer, with L-canavanine.

BACKGROUND

More than 26,000 people die each year in our country from pancreatic adenocarcinoma (1, see numbered references below). Death is the inevitable consequence to more than 90% of patients with this disease. It is the fourth most common cause of cancer death in men and the fifth most common for women (2). Overall, it is the fourth most common carcinoma after those of the lung, colon and breast (3). The incidence of this disease is linear with age to sixty but its occurrence increases markedly in the seventh or eighth decade of life (4). There are several different histologies associated with cancer of the pancreas including small cell cancer, cystadenocarcinoma, islet cell tumors, lymphoma and carcinoid; however, 75–80% of the cases involve adenocarcinomas of ductal origin (5). The only definitive risk factor in pancreatic cancer is cigarette smoking. A typical smoker accepts up to four times the risk of a nonsmoker (6).

Located in the upper abdomen in the retroperitoneum, the pancreas is associated intimately with many major structures including the portal vein, stomach, duodenum, common bile duct and the superior mesenteric artery. As the tumor grows, the patient's symptoms result from tumor infiltration of surrounding structure causing pain, nausea, vomiting, weight loss and jaundice. The latter condition presents symptoms in no more than one half of the patients. Once tumor infiltration occurs other structures such as the portal vein become affected and this precludes curative resectioning of the pancreas.

Effective treatment of pancreas cancer must achieve two difficult goals: control of the primary tumor mass, both initially and subsequently, and treatment of the metastatic tumor cells. As a result of its insidious onset, the diagnosis of pancreas cancer is delayed frequently for several months. This delay has profound implications, since metastatic spread to the liver or lymph nodes has been observed at a time of diagnosis in 60% of patients, and this factor diminishes the prospect for long-term survival (7). Also, there are no known specific markers of carcinoma of the pancreas and it is asymptomatic in its early stage (8).

Conventional Therapy for Pancreatic Cancer

Currently, surgery is the primary and only curative therapy for pancreas cancer. However, only 15–25% of tumors are resectable at the time of diagnosis (9) and regrettably only 10–20% of patients resected will survive more than two years (10). With these less tan satisfactory surgical results, present day therapy has evolved in two directions: palliation of symptoms and aggressive multimodality treatment regime's which combines surgery with chemotherapy and radiation treatment.

Palliative therapy has become a major thrust of current treatment. Initial relief of symptoms has relied on surgery with surgical bypass of gastric outlet obstruction (11) and operative bypass of biliary obstruction (12). Subsequent symptomatic treatment has centered around endoscopic placement of biliary stents to bypass tumors blocking the biliary tract (13) and/or percutaneous placement of bypass conduits (14).

Aggressive multimodality therapy combining chemotherapy and radiation therapy which surgery has been the response of choice when surgery alone was not effective. Radiation has been the cornerstone of therapy for unrespectable cancer of the pancreas and 5-fluorouracil (5-FU) chemotherapy has been for an important adduct to radiation treatment in these patients (15). However, despite these valiant efforts, no patient survives five years.

A single, small randomized trial showed significant benefit from combined radiation and chemotherapy given two years after operation (16). While this study was limited by an inadequate number of patients, none the less there was benefit to patients receiving multi-modality treatment.

Effective radiotherapy needs to maximize exposure of the affected tissues while sparing normal surrounding tissues. Interstitial therapy, where needles containing a radioactive source are embedded in the tumor, has become a valuable new approach. In this way, large doses of irradiation can be delivered locally while sparing the surrounding normal structures (17). Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures. Despite the obvious advantage of approaches predicated upon local control of the irradiation, patient survival is not significantly improved (18, 19).

The foundation of chemotherapy for carcinoma for the pancreas has employed 5-FU(20). Here too, the prognosis is bleak; no better than 10–15% of patients treated with 5-FU will experience a significant reduction in tumor size; overall survival rates are not improved. The addition of other chemotherapeutic agents such as cis-platin or adriamycin has not dramatically improved disease management (20). For this reason, attempts to augment the intrinsic activity of 5-FU have been undertaken. On one approach, 5-FU is converted to 4-fluorodeoxyuridine monophosphate (FdUMP) which binds covalently to thymidylate synthase (EC 2.1.1.45). This competitive inhibitor disrupts DNA replication by curtailing deoxyuridine monophosphate anabolism to deoxythymidine.

Reduced folates such as leucovorin are a necessary cofactor for FdUMP binding to thymidylate synthase (21). Cancer cells depauperate in reduced folate are resistant to 5-FU chemotherapy but that resistance can be circumvented by providing exogenous reduced folate (22). While 5-PU plus leucovorin relative to 5-FU alone has proven efficacious in treating colon cancer, patients with pancreas cancer received no benefit by providing these two drugs in combination (23).

5-Fluorouracil can also be converted to 5-fluorouridine monophosphate which can be incorporated into mRNA thereby affecting protein translation. N-N-(phosphonacetyl)-L-aspartic acid (PALA) inhibits the transformation of aspartic acid to orotidine monophosphate which is converted subsequently to uridine monophosphate. The use of PALA provides a means of depleting essential uridine monophosphate. In the absence of uridine monophosphate, fluorouridine monophosphate is incorporated preferentially into mRNA which promotes cell death. Preliminary data from experiments employing high dose (2,600 mg/m$^2$) 5-FU after pretreatment with PALA have been promising as significant tumor reduction has been noted in 5 of 6 patients (24). However, subsequent phase II data have been less positive (25) with only one patient in 29 achieving any benefit.

While new experimental efforts in treating pancreas cancer have been initiated, their limited success emphasizes the need for radically new approaches in the management of this devastating disease. The present invention provides an additional alternative for the treatment of cancers, particularly pancreatic cancer by providing for a pharmaceutical composition comprising canavanine, and a method treatment of cancer, particularly pancreatic cancer with canavanine.

DISCLOSURE OF THE INVENTION

The present invention provides a method of treating pancreatic cancer by administering a pharmaceutically effective amount of a composition comprising L-canavanine to a patient with pancreatic cancer.

The invention also provides a pharmaceutical composition comprising a pharmaceutically effective amount of a composition comprising L-canavanine.

In an alternative embodiment the invention provides pharmaceutical composition comprising canavanine and 5-fluorouracil.

In still another embodiment the invention provides a pharmaceutical composition comprising canavanine and a compound selected from the group consisting of (S)-2-aminoethyl-L-cysteine, L-2-azetidine carboxylic acid, L-selenomethionine, L-3-[N-hydroxy-4-oxypyridyl]-2-aminopropionic acid and mixtures thereof.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

The invention provides a pharmaceutical composition comprising canavanine, and a method treatment of cancer, particularly pancreatic cancer with canavanine. A depiction of the canavanine molecule appears below.

In addition to the amino acids which are the building blocks of proteins, living systems also produce about 750 nonprotein amino acids (26). These compounds possess a rich structural diversity and often elicit deleterious biological effects in viruses and all living systems (27), L-Canavanine, the L-2-amino-4-(guanidinoxy) butyric acid structural analog of L-arginine, is such a higher plant toxicant. Produced and stored by leguminous plants, canavanine is part of their chemical defense, where it functions as a barrier against a wide array of insects and other pests (28, 29).

Biochemical Basis for Canavanine's Antimetabolic Properties

Studies with larvae of the tobacco horn worm, Manduca sexta, reveal that canavanine is an effective substrate for arginyl-tRNA synthetase. This canavanine-sensitive insect replaces on average at least one of three arginyl residues with canavanine in the de novo synthesized proteins of the hemolymph and body wall (30).

Figure 1:
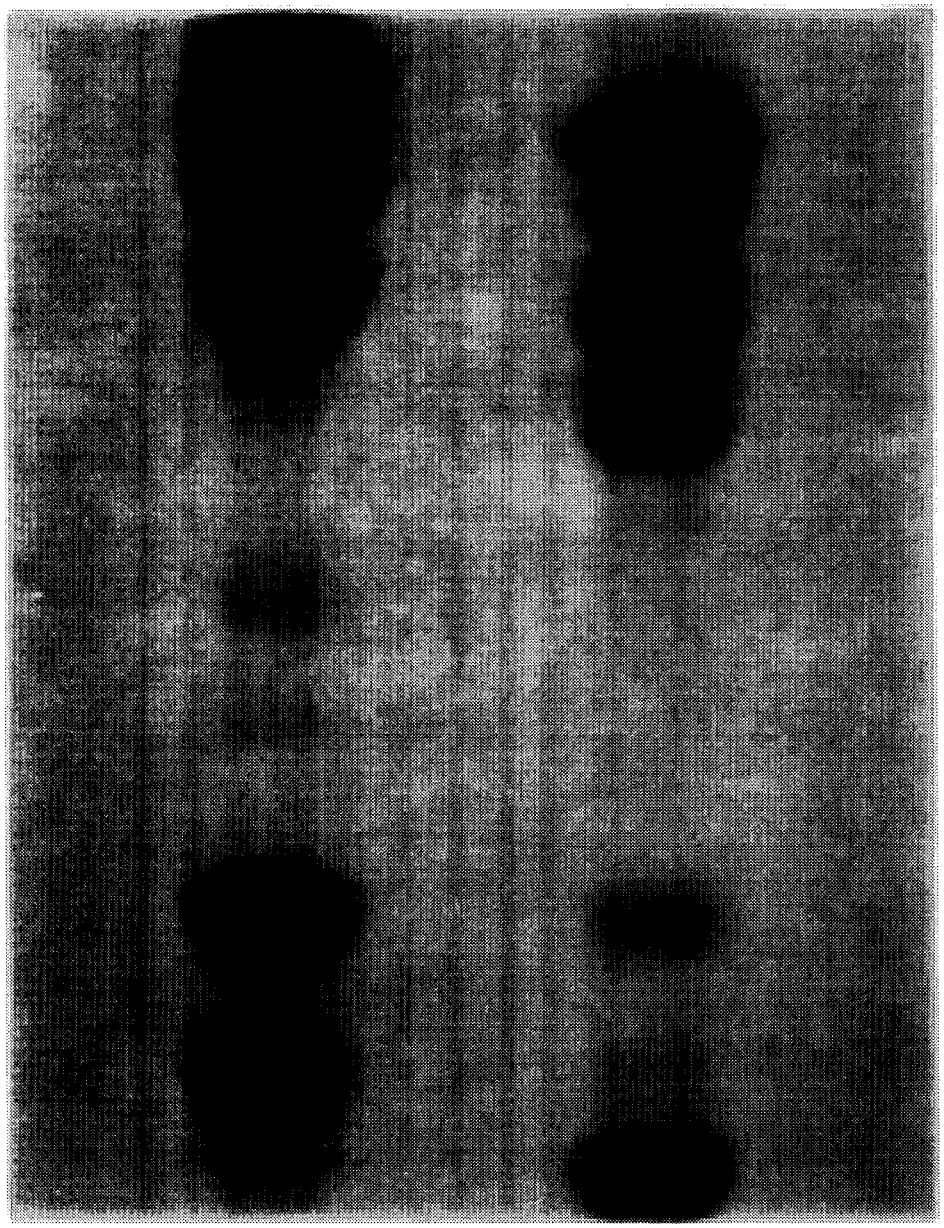
FIG. 1 shows electrophoretic evidence of structural change caused by canavanine. Vitellogenin was examined by gradient polyacrylamide electrophoresis as described elsewhere.

Vitellin, an essential egg protein, is constructed by the gravid migratory locust, Locusta migratoria migratorioides [Orthoplera] from amino acids released by degradation of vitellogenin (31). Administration of canavanine to the female locust produces a canavanyl vitellogenin in which 18 of the nearly 200 arginine residues are replaced by canavanine (31); thus, canavanine occurs about once every 225 amino acids. In spite of this paucity in canavanine content, it elicits a profound alteration in vitellogenin structure best observed by electrophoretic analysis (FIG. 1).

Other chemical, physical, biochemical, and immunological tests confirm the dramatic change in the three dimensional conformation resulting from canavanine assimilation into this protein (31).

In response to microbial infection or mechanical injury, larvae of the meat-eating fly, *Phormia terranovae,* generate a group of antibacterial proteins known trivially as the diptericins. If canavanine is included at the time of mechanical injury, it is incorporated into newly produced diptericins (32). Analysis of the diptericin activity of arginine- or canavanine-treated larvae reveals a nearly total loss of detectable biological activity for 3 of the 4 protective proteins-only diptericin A displays biological activity. Thus, canavanine incorporation into these protective proteins in place of arginine curtails severely their biological activity.

*Manduca sexta* larvae respond to injected fragments of the cell wall of *Micrococcus lutea* by producing lysozyme (EC 3.2.1.17), a protein which cleaves the mucopolysaccharide framework of the cell wall. Administration of 1 mg canavanine $g^{-1}$ fresh larval weight at the time of bacterial challenge generates canavanyl lysozyme with a ratio of canavanine to arginine of 1:3.8±0.2(33). Canavanyl lysozyme exhibits a 50% loss of catalytic activity (33). These insectan studies support out contention that the antimetabolic effects of canavanine reflects its incorporation into newly synthesized proteins which alters essential conformation and produces dysfunctional proteins.

Canavanine may be produced by isolated the amino acid from jack beans by the method of Kitagawa, Tokiyama, J. Biochem., (Tokyo) 11, 265 (1929) incorporated herein by reference in its entirety. See also Nyberg et al., J. Am. Chem. Soc., 79, 1222 (1957); Frankel et al., J. Am Chem. Soc., 3127 (1963); and Yamada et al., Agr., Biol. Chem., 37, 2201 (1973) for additional methods of synthesis of canavanine, also incorporated herein by reference.

Evaluation of Canavanine's Antineoplastic Activity

Canavanine's ability to disrupt the growth of rapidly dividing and growing larval cells led to whole animal studies of its antineoplastic activity. The inventors found that canavanine may be incorporated into key protein(s) unique to the cancer cell and that these structurally aberrant proteins, critical to the growth and proliferation of the cancer cell, may be dysfunctional.

EXAMPLE 1

Employing a solid rat colonic carcinoma in Fischer F433 rats, it was demonstrated that canavanine possesses appreciable antineoplastic activity. For example, administration of canavanine at a 3.0 g/kg dosing regimen for 5 consecutive days results in a 22% loss in tumor volume, while 9 days of daily dosing elicits a 60% diminution of the tumor (34).

However, canavanine's is cumulatively toxic and can result in a weight loss of 19% in animals dosed with 3.0 g/kg canavanine for 5 days (34). Additional experimentation established unequivocally that the observed body weight loss is not responsible for canavanine's antitumor effects (34).

EXAMPLE 2

Initial experimental efforts have been extended to determine if canavanine's efficacy as an anticancer agent is increased in combination with 5-fluorouracil (5-FU). Providing canavanine at 1.0 g/kg or 2.0 g/kg daily for 5 consecutive days with 5-FU increases significantly the antitumor activity of either drug alone (see FIG. 2). Body weight loss experienced by canavanine-treated animals increases in those animals given both drugs. These studies evidence that combination therapy offers a viable means of improving canavanine's intrinsic efficacy.

In order to improve canavanine's potential as a chemotherapeutic agent, a number of canavanine derivatives were evaluated for enhanced antitumor efficacy and diminished growth-inhibiting activity.

Enzyme activity studies conducted, reveal a number of other nonprotein amino acids whose assimilation into proteins disrupts normal catalytic activity. Some natural products such a (S)-2-aminoethyl-L-cysteine, L-2-azetidine carboxylic acid, L-selenomethionine, and L-3-[N-hydroxy-4-oxypyridyl]-2- aminopropionic acid or mixtures thereof are not only very active but also interact with canavanine to significantly amplify canavanine-mediated disruption of protein function (35).

Thus, there are a number of nonprotein amino acids beside canavanine able to substitute for their protein amino acid counterpart to generate dysfunctional proteins. These natural products often possess significant antitumor potential alone, in combination with canavanine, and with other therapeutic drugs.

The ability to assault the local cancer cell and even its metastatic offspring simultaneously with an array of nonprotein amino acid derivatives offers a weapon of considerable potential value.

Canavanine's Efficacy against Pancreatic Tumor

Analysis of L-[guanidinoxy-$^{14}$C] canavanine uptake into the protein of the major organs of the rat disclosed the highest radiolabeling in pancreatic proteins (36). These proteins had 10 times the amount found in liver, muscle or brain samples. The efficient incorporation of radiolabeled canavanine into pancreatic proteins coupled with its demonstrated ability to create dysfunctional proteins prompted evaluation not only of canavanine but more importantly its derivatives as chemotherapeutic agents for human pancreas cancer.

A basic understanding of the biochemical basis for canavanine's antimetabolic properties has emerged over the past five years and these efforts have permitted development of a sound rationale for derivative synthesis. Chemical synthetic efforts, detailed herein, hold the promise of providing drugs with markedly enhanced efficacy and permit their administration at significantly lower dose levels than those required by canavanine. It has been unequivocally established that a 1 g kg$^{-1}$ dose of canavanine has no adverse effect on body weight nor on other discernible parameters of the rat.

A chemotherapeutic strategy predicated upon controlling cancer cell growth through the formation of structurally aberrant, dysfunctional proteins has been developed. Such macromolecules deny the cancer cell essential metabolites, undermine regulatory and other cellular control elements and pervasively disrupt critical cellular growth-related processes. Current treatment practices have not enjoyed substantial success and a radical new approach is justified. The approach of the invention is one with a strong biochemical foundation that provides a sound rationale for the development of new derivatives for use as chemotherapeutic agents. Most importantly, canavanine's mode of actions is snot directed at DNA replication, events that occur prior to transcription of the message, nor at message translation.

The present strategy for developing an effective chemotherapeutic agent does not focus on nucleic acid metabolism but rather at the level of protein function.

Evaluation of Drug Efficacy

A number of cell lines derived from pancreatic ductal adenocarcinoma have been established, including CFPAC-1 (ATCC CRL 1918), PANC-1 (ATCC CRL 1469), MIA-PaCa- 1, and MIA-PaCa-2 (ATCC CRL 1420). MIA-PaCa2 is highly tumorigenic, has lost the ability to be growth regulated, and is derived from metastatic cells. CFPAC- 1, which is derived from a primary tumor line, is the faster growing cell line and is preferable for whole animal studies. The availability of each of these lines from the American Type Culture Collection, 12301 Parklawn Drive, Rockville, Md., U.S.A., insures an effective means for initial screening of newly synthesized derivatives both alone and in combination with other developed compounds as well as with drugs employed presently inhuman chemotherapy. The most promising candidates are employed in whole animal evaluation involving nude mice.

This invention permits an effective transition from laboratory findings and evaluations to their beneficial employment in alleviating the human suffering associated with this dreadful disease.

EXAMPLE 3

Antitumor Effect of Canavanine in the Male Fischer Rat

Figure 2:
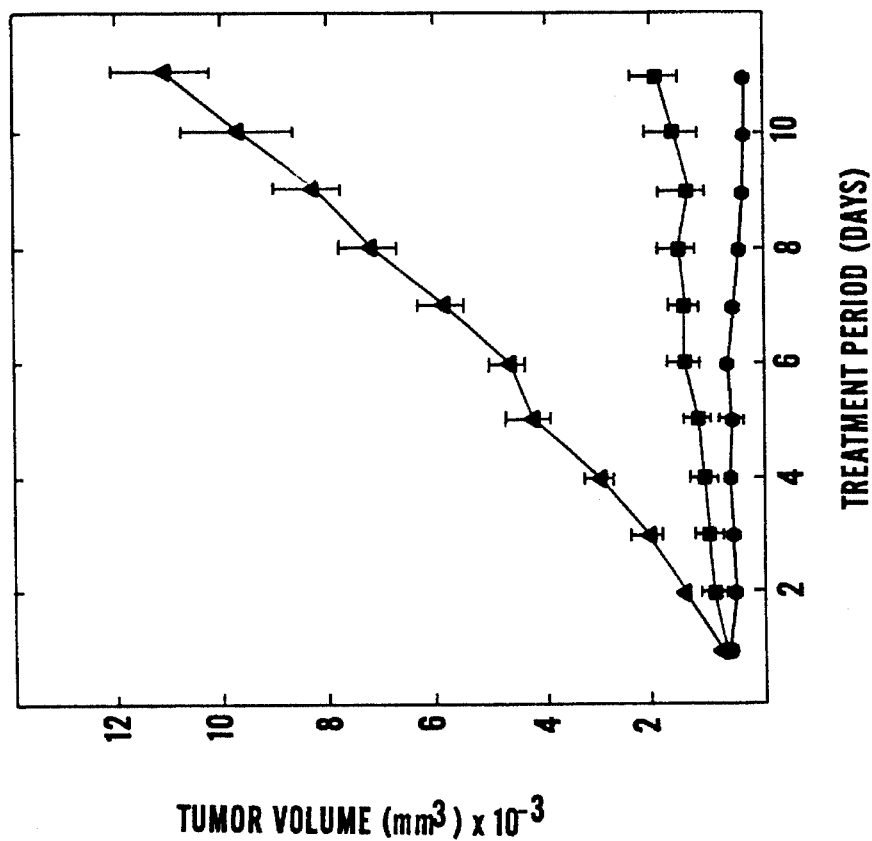
FIG. 2 shows tumor growth in male Fischer rats following administration of canavanine, 2.0 (closed rectangle) or 3.0 (closed circle) g/kg for 9 days. Control animals (closed triangle) receive 0.95 received 0.95 (w/v) NaCl. The standard error bar was omitted if within the area occupied by the data point, n=5 S.E.M.

The marked antitumor effect of L-canavanine was demonstrated initially by our research group in studies on a solid, colonic carcinoma in male Fischer 344 rats. Administration of 3 g/kg canavanine sc reproducibly prevented tumor growth during 5 or 9 consecutive treatment days. In fact, the final fresh tumor weight was typically 10% less than the weight of the initial tumor (34) (FIG. 2).

Figure 3:
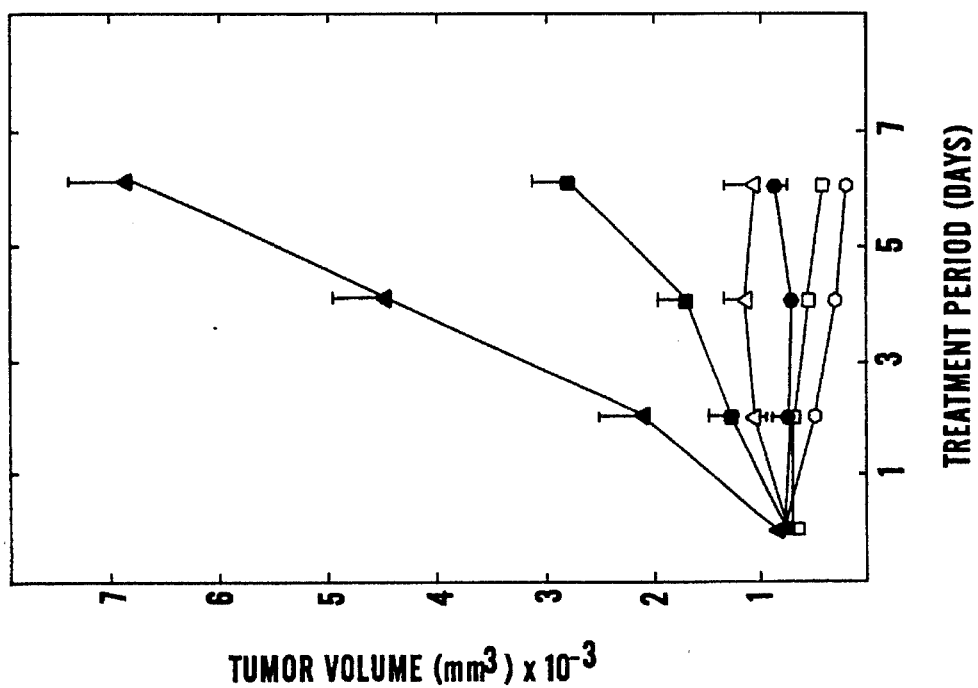
FIG. 3 shows tumor growth in male Fischer rats following 5 daily sc injections of 35 mg/kg 5-FU (closed circle) 2.0 g/kg canavanine (closed square), 1.0 g/kg canavanine (open triangle), 35 mg kg 5-FU plus 2.0 g/kg canavanine (open circle) or 35 mg/kg 5-FU plus 1.0 g/kg canavanine (open square). Control animals (closed triangle) received 0.95 (w/v) NaCl. The S.E. bar was omitted if it fell within the area occupied by the data point, n=5 S.E.M.

To enhance canavanine's antineoplastic activity, it was tested in combination with 5-FU (FIG. 3). Providing canavanine at 1.0 g/kg or 2.0 g/kg daily for 5 consecutive days with 5-FU increased significantly the antitumor activity of either drug alone. This whole animal study was of considerable importance because it demonstrated that combination therapy offers a viable mean of improving canavanine's intrinsic efficacy and supports our contention that canavanine and its derivatives in conjunction with 5-FU may offer an effective chemotherapeutic strategy. Alternatively, canavanine therapy may be combined with radiotherapy.

EXAMPLE 4

The Effect of Canavanine on MIA-PaCa-I Cells.

Figure 4:
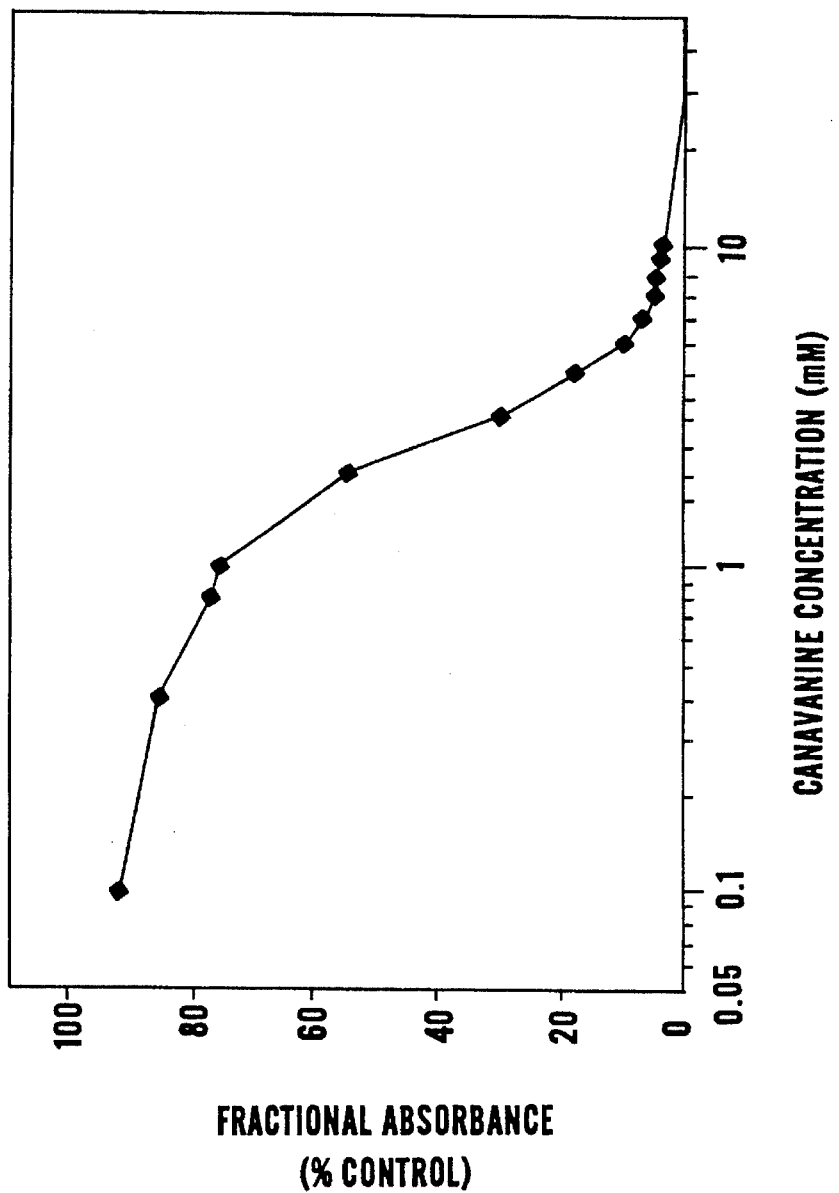
FIG. 4 shows MIA-PaCa-1 cells were exposed to the indicated level of canavanine for 3 days in Dulbecco's modified media containing 0.4 mM arginine. Each point represents the means from an experiments. The standard error bar was omitted when it fell within the area occupied by the data point.

Work has been performed to evaluate the effect of canavanine on MIA-PaCa-1 cells. Cell survival was determined by the ability of viable cells grown on Dulbecco's modified medium to reduce tetrazolium dye to a colored formazan product. The experiment depicted in FIG. 4 discloses dramatically the potent efficacy of canavanine against these cells.

Figure 5:
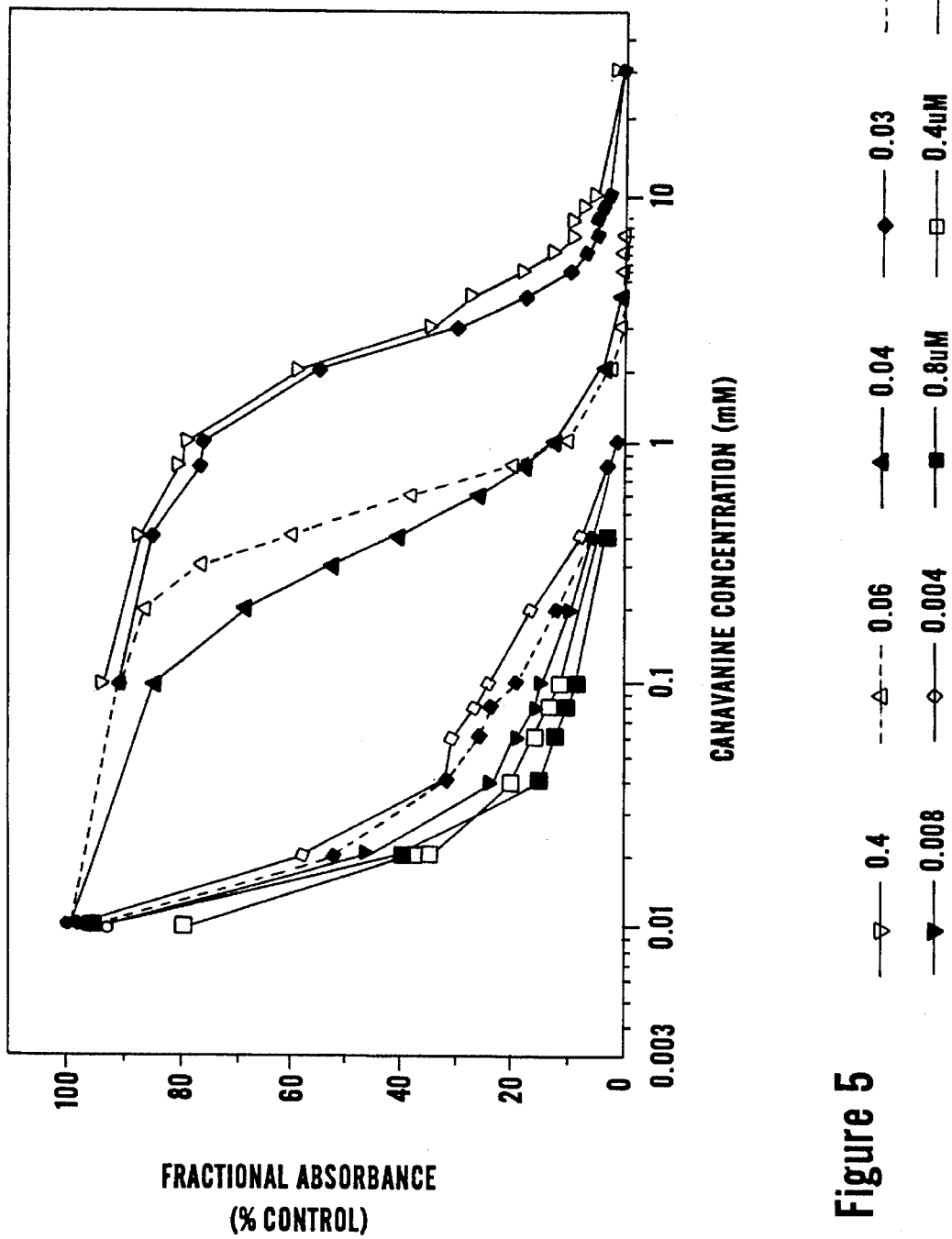
FIG. 5 shows MIA-PaCa-1 cells were exposed to various amounts of canavanine with the indicated level of arginine to generate this family of curves.

That the antitumor potential of canavanine is related directly to the competing arginine concentration is depicted in FIG. 5. This finding is of great importance because it reveals that canavanine is functioning as an effective arginine antagonist. This point is seminal to our contention that the antitumor effect of canavanine is related to its competition with arginine for arginyl-tRNA synthetase.

EXAMPLE 5

The Antineoplastic Effect of Canavanine in the Nude Mouse

Figure 6A:
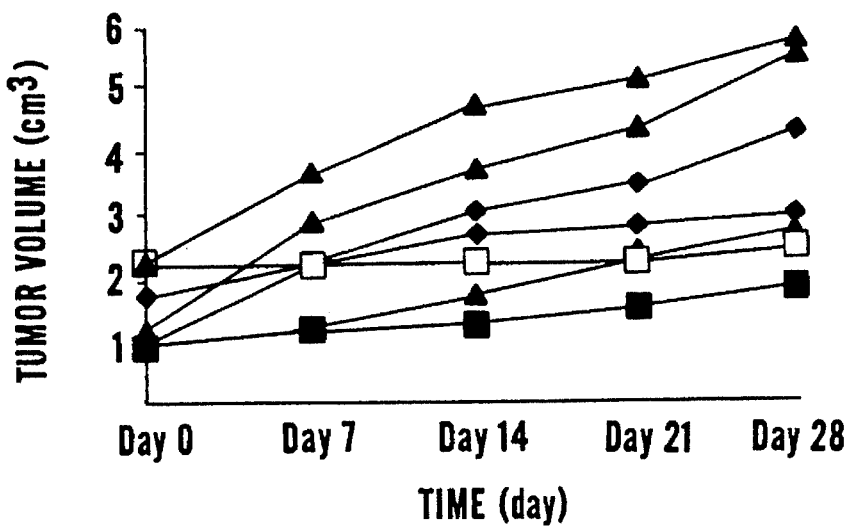
FIG. 6A and 6B show Mice tumor volume ($cm^3$) of control mice (A) and canavanine-treated mice (B). Canavanine-treated animals were injected daily with 4 g/Kg of drug in sterile saline, control animals receive 0.9% (w/v) NaCl.
Figure 6B:
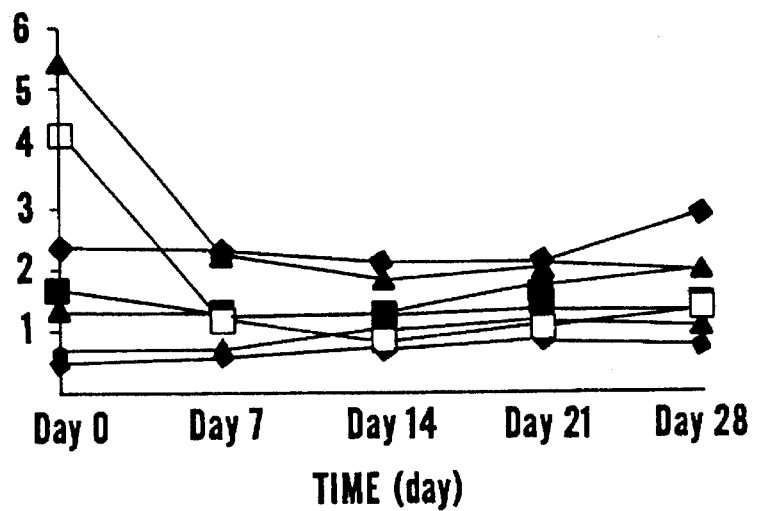

Experimental effects with athymic nude mice were conducted with 6 treated and control mice. The palpable CFPAC-1-derived tumors grew slowly but after 28 days appreciable tumor growth had occurred in all experimental animals (FIG. 6A). By contrast, the CPFAC-1-derived tumors exhibited little growth in canavanine-treated animals (FIG. 6B). In 2 of the 7 experimental animals, a precipitous decline in tumor volume was observed during the first treatment week. These exciting experimental results add further support to the fact that canavanine and its derivatives possess considerable potential for the treatment of human pancreatic carcinoma.

Further, the compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient.

For oral administration either solid or fluid unit dosage forms can be prepared. The compounds are useful in pharmaceutical compositions (wt %) of the active ingredient with a carrier or vehicle in the composition in about 0.01 to 99% and preferably about 5 to 15%.

Either fluid or solid unit dosage forms can be readily prepared for oral administration. For example, the compounds can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixir.

Pharmaceutical compositions for parenteral administration can also be obtained using techniques standard in the art as set forth in *Remington's Pharmaceutical Sciences*, 18th Ed., 1989, Mack Publishing Company, incorporated herein by reference it its entirety.

Accordingly, compositions suitable for administration are particularly included within the invention. Parenteral solutions or suspensions may be administered. If desired, a more concentrated slow release form may be administered. Accordingly, incorporation of the active compounds in a slow release matrix may be implemented for administering transdermally. The compounds may preferably be administered at about 1 to 20% of the composition and more preferably about 5 to 15% wt % of the active ingredient in the vehicle or carrier.

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 0.1 to 50 mg per kilogram of the subject's weight administered per day. Preferably about 25 to 50 mg per kilogram body weight is administered a day. The required dose is less when administered parenterally, preferably about 25–30 mg per kilogram of body weight per day may be administered intramuscularly.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

REFERENCES

1. Douglass HO, Tepper J, Leichman L. Neoplasms of the bile duct and pancreas, in: *Cancer Medicine.* Holland JF, Frei et al. eds. Third edition: Lea and Febiger, 1993.

2. Cited in reference 1.

3. Cited in reference 1.

4. Wynder EL. Cancer Res 35: 2228, 1975.

5. Kissane JM. J Surg Oncol 7: 167, 1975.

6. MacMahon B. Cancer 50: 676, 1982.

7. Hermanek P. Eur J Surg Oncol 17: 167, 1991.

8. Cited in reference 1.

9. Moosa AR. Cancer 50: 2689, 1982.

10. Appelquist P et al. J Surg Oncol 23: 143, 1983.

11. Singh SM et al Ann. Surg 212: 132, 1990.

12. McGrath PC et al. Ann Surg 209: 21, 1984.

14. Speer AG et al. Lancet 11: 7, 1987.

15. Tepper J et al. Cancer 37: 1519, 1976.

16. Gatrointestinal tumor study group. Arch Surg 120: 99, 1985.

17. Tepper JE. In: *Cancer of the bile duct and pancreas.* Preeco PE. et al., eds) WB Saunders Co., Philadelphia, 1989.

18. Sindelar WF & Kinsella TJ. Int J Radiat Oncol Biol Phys 12 (suppl 1): 48, 1986.

19. Abe M & Takahashi M. Int J Radiat Oncol Biol Phys 7: 863, 1981.

20. Moertel CG et al. Surg 85: 509, 1979.

21. Evans RM et al. Cancer Res 41: 3288, 1981.

22. Keyomarski K & Moran RG. Cancer Res 46: 5529, 1985.

23. Crown J et al. J Clin Oncol 9: 1682, 1991.

24. Ardalan B & Singh G. J Clin Oncol 6: 1053, 1988.

25. Nagourney RA et al. Proc Am Soc Clin Oncol 13: 636, 1994.

26. Rosenthal GA. *Plant Nonprotein Amino and Imino Acids. Biological, Biochemical, and Toxicological Properties,* Academic Press, San Diego, 1982.

27. Rosenthal GA. Q Rev Biol 52: 155, 1977.

28. Rosenthal GA. In: *Insecticides: Mechanism of Action and Resistance* D. Otto & B. Weber, eds, Intercept Ltd., Andover, England, 1982.

29. Rosenthal GA. In: *Frontiers and New Horizons in Amino Acid Research,* K. Takai, ed. Elsevier, New York, 1992.

30. Rosenthal GA. Phytochemistry 30: 1055, 1991.

31. Rosenthal GA et al. J Biol Chem 264: 13693, 1989.

32. Rosenthal GA et al. J Biol Chem 264: 9768, 1989.

33. Rosenthal GA & Dahlman DL. J Biol Chem 266: 15684, 1991.

34. Thomas DA. et al. Cancer Res 46: 2898, 1986.

35. Rosenthal GA. Unpublished experimental results.

36. Thomas DA & Rosenthal GA. Toxicol & Appl Pharm 91: 406, 1987.

We claim:

1. A method of treating pancreatic cancer comprising the steps of administering a pharmaceutically effective amount of a composition comprising canavanine to a patient with pancreatic cancer.

2. A method of treating pancreatic cancer according to claim 1 wherein said canavanine is L-canavanine.

3. A method of treating pancreatic cancer according to claim 1 wherein said composition further comprises 5-fluorouracil.

4. A method of treating pancreatic cancer according to claim 1, wherein said composition further comprises a compound selected from the group consisting of (S)-2-aminoethyl-L-cysteine, L-2-azetidine carboxylic acid, L-selenomethionine, L-3-[N-hydroxy-4-oxypyridyl]-2-aminopropionic acid and mixtures thereof.

5. A method of treating pancreatic cancer according to claim 1, wherein said pharmaceutically effective amount is about 25 to 50 mg per kilogram body weight a day.

6. A pharmaceutical composition consisting essentially of canavanine and 5-fluorouracil.

7. A pharmaceutical composition consisting essentially of canavanine and a compound selected from the group consisting of (S)-2-aminoethyl-L-cysteine, L-2-azetidine carboxylic acid, L-selenomethionine, L-3-[N-hydroxy-4-oxypyridyl]-2-aminopropionic acid and mixtures thereof.

* * * * *